(12) United States Patent
Meister (10) Patent No.: US 9,919,155 B2
(45) Date of Patent: Mar. 20, 2018

(54) STIMULATION CHANNEL CONDITIONING (75) Inventor: Dirk Meister, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 728 days.

(21) Appl. No.: 12/691,912

(22) Filed: Jan. 22, 2010

(65) Prior Publication Data

US 2010/0191308 A1    Jul. 29, 2010

Related U.S. Application Data

(60) Provisional application No. 61/146,787, filed on Jan. 23, 2009.

(51) Int. Cl.
*A61N 1/36* (2006.01)
*A61N 1/05* (2006.01)

(52) U.S. Cl.
CPC ........ *A61N 1/36036* (2017.08); *A61N 1/0541* (2013.01)

(58) Field of Classification Search
CPC .......................... A61N 1/36032; A61B 5/4041
USPC .................................................... 607/57, 137
See application file for complete search history.

(56) References Cited

U.S. PATENT DOCUMENTS

| 4,592,359 | A | 6/1986 | Galbraith ...................... 128/419 |
| 7,171,261 | B1 * | 1/2007 | Litvak ................ A61B 5/04001 600/544 |
| 8,660,647 | B2 * | 2/2014 | Parnis et al. ..................... 607/42 |
| 2004/0082980 | A1 * | 4/2004 | Mouine et al. ................. 607/48 |
| 2004/0158170 | A1 * | 8/2004 | Overstreet et al. ........... 600/554 |
| 2005/0101878 | A1 * | 5/2005 | Daly et al. ..................... 600/559 |
| 2006/0149337 | A1 * | 7/2006 | John .............................. 607/45 |
| 2006/0235490 | A1 * | 10/2006 | Killian et al. .................. 607/60 |
| 2006/0247735 | A1 | 11/2006 | Honert ........................... 607/57 |
| 2007/0043400 | A1 * | 2/2007 | Donders et al. ............... 607/45 |
| 2009/0018614 | A1 | 1/2009 | Zierhofer ........................ 607/56 |
| 2009/0088817 | A1 | 4/2009 | Starkebaum et al. .......... 607/40 |
| 2009/0132006 | A1 * | 5/2009 | van den Honert et al. ... 607/57 |
| 2009/0264961 | A1 | 10/2009 | Schleich et al. ............... 607/57 |

FOREIGN PATENT DOCUMENTS

WO    WO 99/35882    7/1999    ............. H04R 25/00

OTHER PUBLICATIONS

European Patent Office, International Search Report and Written Opinion, PCT/US2010/021718, dated Apr. 29, 2010.

\* cited by examiner

*Primary Examiner* — Michael D Abreu
(74) *Attorney, Agent, or Firm* — Sunstein Kann Murphy & Timbers LLP (57) ABSTRACT

A method is described for delivering stimulation signals in an implantable multichannel neuro-stimulating device such as a cochlear implant. A stimulation channel is selected for delivering a data stimulation signal. One or more desensitization channels spatially adjacent to the stimulation channel are also selected. One or more non-data desensitization signals are delivered on the desensitization channels during a desensitization period before delivery of the data stimulation signal, and then the data stimulation signal is delivered on the stimulation channel. The stimulation channel may be blanked to prevent stimulation signals during a sensitization period before delivering the data stimulation signal.

18 Claims, 6 Drawing Sheets

Desensitization

Sensitization

Desensitization

Desensitization

Fig. 7

STIMULATION CHANNEL CONDITIONING

This application claims priority from U.S. Provisional Patent Application 61/146,787, filed Jan. 23, 2009, which is incorporated herein by reference.

FIELD OF THE INVENTION

The present invention relates to medical implants, and more specifically to signal processing in neuro-stimulation implant systems such as cochlear implants.

BACKGROUND ART

Figure 1:
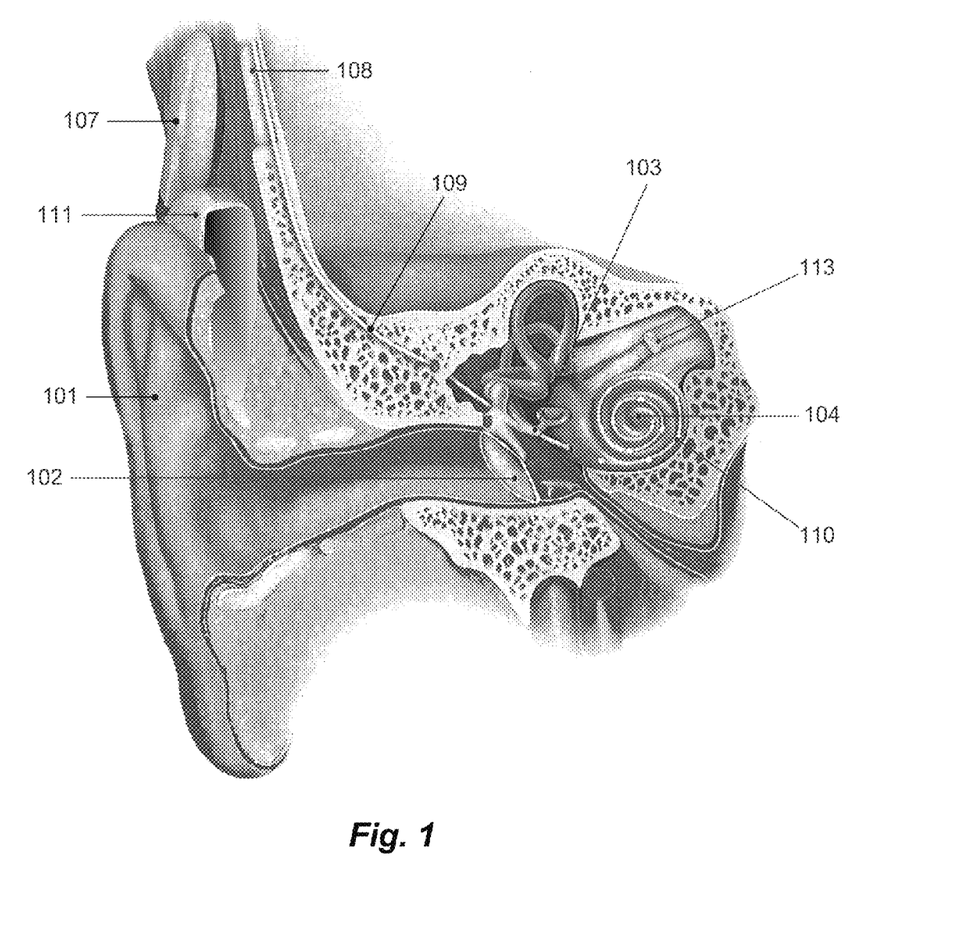
FIG. 1 shows structures in a normal human ear and some components of a typical cochlear implant system.

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implanted stimulation processor 108. Besides receiving the processed audio information, the stimulation processor 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

In cochlear implants today, a relatively small number of electrodes are each associated with relatively broad frequency bands, with each electrode addressing a group of neurons through a stimulation pulse the charge of which is derived from the instantaneous amplitude of the envelope within that frequency band. In some coding strategies, stimulation pulses are applied at constant rate across all electrodes, whereas in other coding strategies, stimulation pulses are applied at an electrode-specific rate.

One problem with cochlear implants is spatial channel interaction where there is considerable geometric overlapping of electrical fields at the location of the excitable nervous tissue when multiple stimulation electrodes are activated the same neurons are activated when different electrodes are stimulated. Spatial channel interaction is primarily due to the conductive fluids and tissues surrounding the stimulation electrode array. Such spatial interaction acts as channel crosstalk which smears audio information across channels and hampers place pitch perception. Up to now the problem of channel interaction has been addressed using coding strategies and/or electrode designs that try to focus the electrical field to the site of stimulation. Such approaches consume a relatively high amount of electrical power.

One prior art approach is known as phased array stimulation, which produces focused stimulation in a medical stimulation device, as described, for example, in U.S. Patent Publication 2006247735, which is incorporated herein by reference. Focused intracochlear electric stimulation is produced using an array of N electrodes: "For each electrode site, N weights are computed that define the ratios of positive and negative electrode currents required to produce cancellation of the voltage within scala tympani at all of the N−1 other sites. Multiple sites can be stimulated simultaneously by superposition of their respective current vectors."

Another prior art approach uses a channel interaction matrix where current spread is reduced by simultaneous pulses on multiple electrodes, as described, for example, in U.S. Pat. No. 7,110,821, which is incorporated herein by reference. Positive and negative amplitudes can occur on different simultaneous stimulated electrodes, resulting in short-circuit currents. The stimulation pattern is calculated by a channel interaction matrix that is derived from telemetry measurements: "The measured or estimated channel interaction is collected or compiled and saved as a channel interaction matrix. The channel interaction matrix is created during a fitting procedure by stimulating one channel at a time while measuring the effects of the stimulation on the neighboring channels. The superposition principal is used, as needed, to determine all the terms of the channel interaction matrix."

U.S. Pat. No. 6,304,787 attempts to diminish current spread by the design of electrode contacts: "In accordance with one important aspect of the present invention, the exposed electrode contacts on the surface of the electrode array have a shape, geometry, or makeup that aids in controlling the current flow and current density associated with the electrode contact as a function of position on the electrode contact. For example, in one embodiment of the invention, the shape or geometry of the exposed electrode contacts is designed to diminish the surface of the electrode contact at the outside edges of the contact, thereby focusing most of the current to flow through the center of the electrode contact."

SUMMARY OF THE INVENTION

Embodiments of the present invention are direct to a method for delivering stimulation signals in an implantable multichannel neuro-stimulating device such as a cochlear implant. A stimulation channel is selected for delivering a data stimulation signal. One or more desensitization channels spatially adjacent to the stimulation channel are also selected. One or more non-data desensitization signals are delivered on the desensitization channels during a desensitization period before delivery of the data stimulation signal, and then the data stimulation signal is delivered on the stimulation channel. During a sensitization period before delivering the data stimulation signal, stimulation signals may be prevented on the stimulation channel, in order to enhance stimulation signals after the end of the sensitization period.

In some specific embodiments, a psychoacoustic model may be used for selecting the stimulation channel. The data stimulation signal may be delivered to an auditory peripheral process and or a central process. The desensitization signals may have an amplitude based on a psychoacoustic model, and/or one or more psychoacoustic measurements. The desensitization signals may form a ramp shaped sequence and/or have an amplitude based on distance from the stimulation channel. The stimulation signal and/or the desensitization signals may be pulse signals.

Embodiments of the present invention include a computer program product in a computer readable storage medium for delivering stimulation signals in an implantable multichannel neuro-stimulating device according to any of the above. Embodiments also include an implantable multichannel neuro-stimulating device having an implantable electrode array having a plurality of stimulation electrodes for stimulating audio nerve tissue with electrode stimulation signals, and a multichannel stimulation module for generating the electrode stimulation signals according to any of the above.

DETAILED DESCRIPTION OF SPECIFIC EMBODIMENTS

Embodiments of the present invention are directed to delivering stimulation signals in an implantable multichannel neuro-stimulating device such as a cochlear implant so as to minimize channel cross-talk by conditioning the channels before a desired stimulus is applied. Two conditioning modes are used: a sensitization mode is applied on the stimulation channel and emphasizes the succeeding stimulation signal, and a desensitization mode attenuates cross-talk signals on channels which are spatially adjacent to the stimulus channel which might arise due to undesired spatial interaction with the stimulus channel.

One specific embodiment is based on neural onset and offset adaptation mechanisms. So-called onset neurons, which are important for encoding the time structure in the auditory pathways, produce action potentials in response to the onset of acoustic signals, Peter Heil and Dexter R. F. Irvine, *First-Spike Timing of Auditory-Nerve Fibers and Comparison With Auditory Cortex*, J Neurophysiol, November 1997; 78: 2438-2454; incorporated herein by reference. Onset neurons exist in the cochlear nucleus and also in more central stages of the auditory pathway, Yidao Cai, JoAnn McGee, Edward J. Walsh, *Processing Of Pitch Information In Complex Stimuli By A Model Of Octopus Cells In The Cochlear Nucleus Computational Models of Auditory Function,* 171 S. Greenberg and M. Slaney (eds.) IOS Press, 2001; incorporated herein by reference. In order to enhance these onsets, the contrast between relevant and non-relevant signals can be increased by "blanking" a certain period (or time) before the relevant signal.

Figure 2:
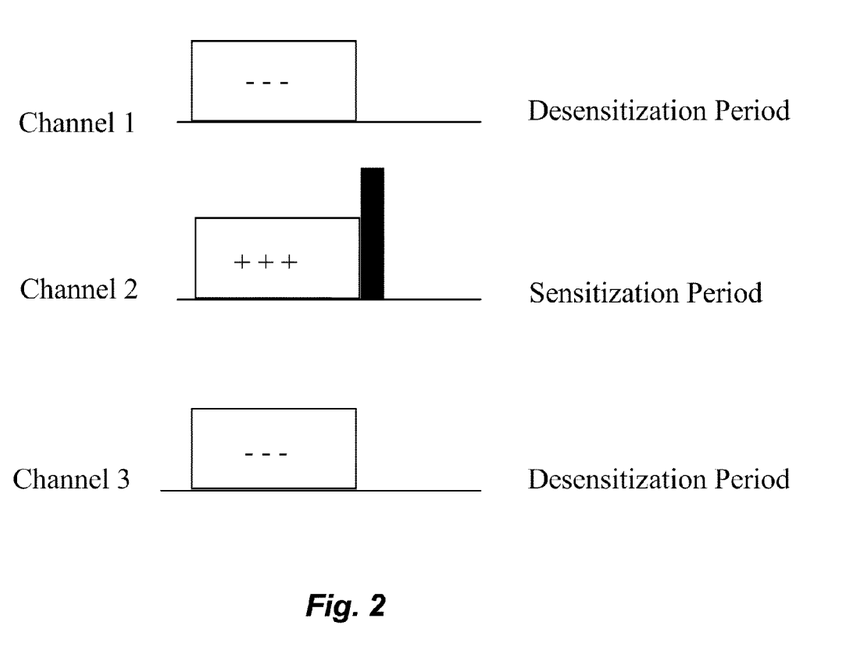
FIG. 2 illustrates the principle of sensitization and desensitization periods.

In FIG. 2, Channel 2 is a stimulation channel that is selected for delivering a data stimulation signal after pre-conditioning during a channel sensitization period. Channels 1 and 3 are spatially adjacent to Channel 2 and are selected as desensitization channels, which are pre-conditioned during corresponding desensitization periods before the delivery of the data stimulation signal on Channel 2. After the channel conditioning periods, the data stimulation signal is delivered on the stimulation Channel 2.

Figure 3:
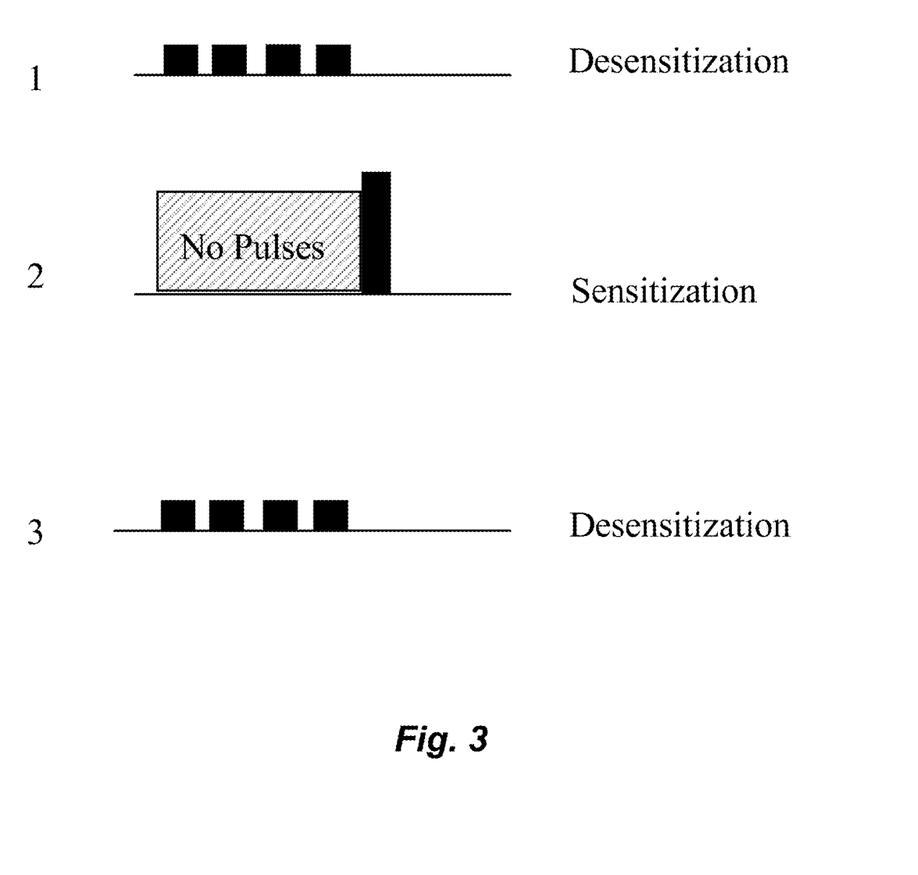
FIG. 3 shows a sequence of desensitization pulses according to one embodiment of the present invention.
Figure 4:
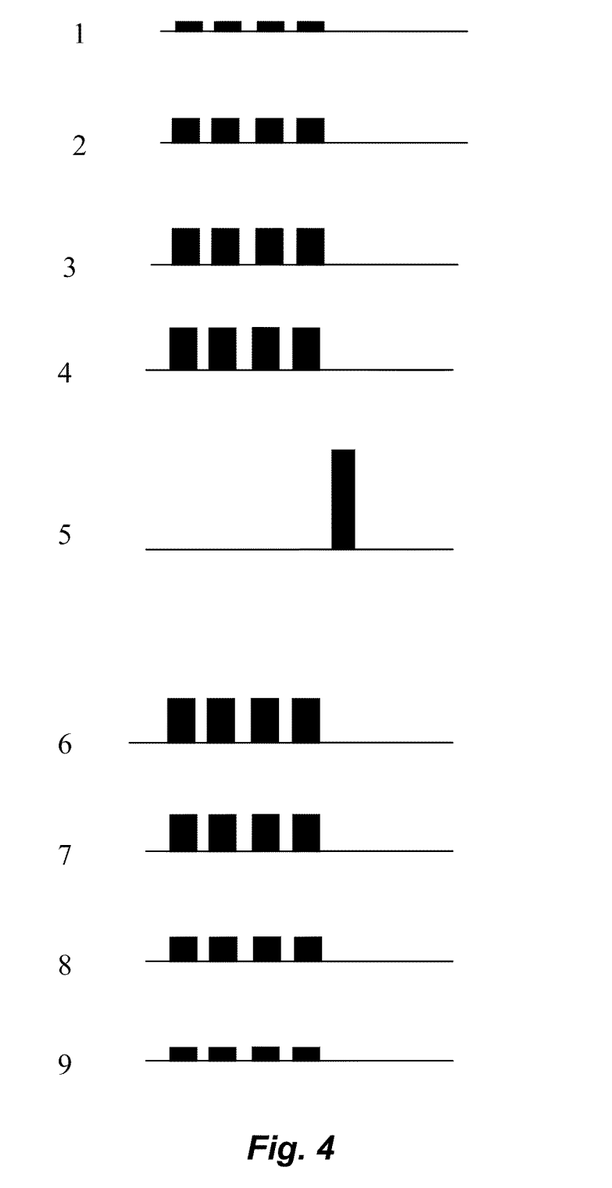
FIG. 4 shows an embodiment using desensitization as a function of channel distance.

For example, FIG. 3 shows that during the channel sensitization period, the stimulation channel is blanked to prevent any stimulation signals before delivering the data stimulation signal. FIG. 3 also shows a series of super- or supra-threshold pulses applied on the neighboring desensitization channels during the desensitization periods before the data stimulation signal (which may also be in the specific form of pulses) is applied on the stimulation channel. Sensitization and desensitization modes can be used with peripheral and/or central processes of the auditory pathway. In some embodiments, the desensitization period may be the same duration on each desensitization channel, as shown in FIG. 3. In other embodiments, different desensitization channels may have individually different durations. And in some embodiments, the desensitization period may correspond to a default state of an electrode. The channel signals (that is, the data stimulation signal and/or the non-data desensitization signals) can be applied in parallel or sequential (interleaved) stimulation modes. The number of neighboring desensitization channels can be selected individually, either based on a model or on patient specific measurements. The signal level of the desensitization signals can be derived based on a model such as a psychoacoustic model, or by measurements such as psychoacoustic measurements. As shown in FIG. 4, the signal levels of the desensitization signals can be derived as a function of spatial distance of the desensitization channel from the stimulation channel.

Figure 5:
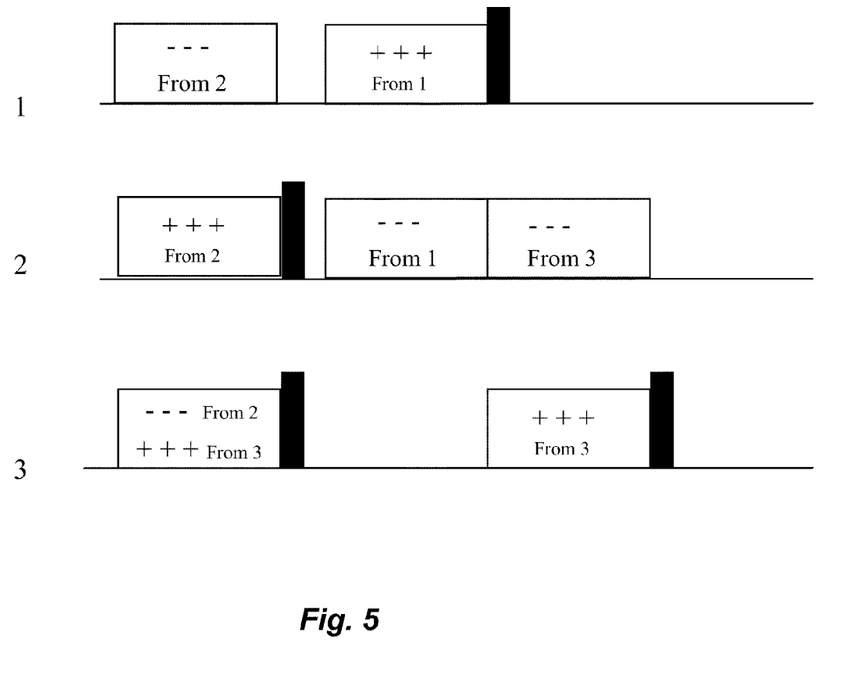
FIG. 5 shows a combination of stimuli on multiple channels.
Figure 6:
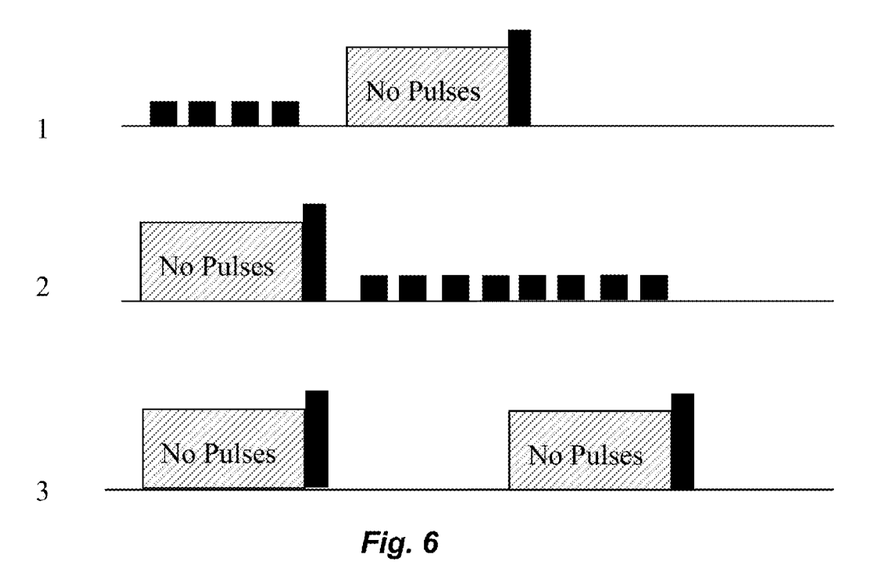
FIG. 6 shows applied pulses for stimuli on multiple channels.

In some embodiments, stimulation signals may be applied on multiple channels at or around the same time. In such circumstances, the sensitization periods may be defined first for each stimulation channel. In FIG. 5, this is illustrated with a "+++" sensitization period on Channel 3 which pre-conditions that channel for a desired stimulation pulse, but which overlaps with a desensitization period ("---") originating from Channel 2. To deal with such a situation, there may be a rule that sensitization periods have priority over the desensitization periods, and then the remaining desensitization periods can be set up. FIG. 6 shows the resulting channel signals from such an embodiment. These conflicts can be minimized, if a (psychoacoustic) masking model is applied before setting up the sensitization periods.

Figure 7:
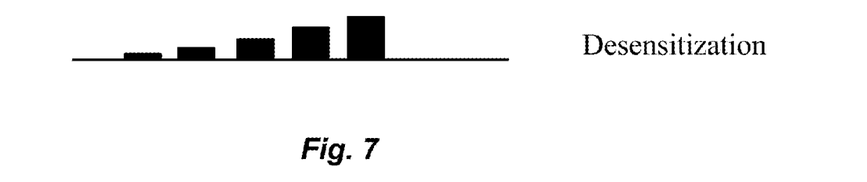
FIG. 7 shows ramped desensitization pulses.

To minimize perception of the desensitization signals by the patient, an embodiment may shape the desensitization signals such as into a sequence of ramped pulses as shown in FIG. 7. The amplitudes of these pulses can be determined with psychoacoustic measurements, so that they are not perceptible or almost not perceptible for the implant patient.

In embodiments of the present invention, only low level threshold pulses with relatively little energy are applied as desensitization signals, whereas the prior art methods required a relatively high amount of energy for channel separation. The channel blanking during the sensitization periods also results in fewer stimulation pulses and therefore consumes less electrical power. In addition, embodiments operate on a perceptual level changing the amount of information that is transferred by the neurons.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of delivering stimulation signals in a multi-channel cochlear implant system, the cochlear implant system including a microphone, an implantable electrode array having a plurality of stimulation electrodes for stimulating audio nerve tissue with electrode stimulation signals, and a multichannel stimulation module for generating the electrode stimulation signals, the method comprising:
    providing, by the microphone, an audio signal input;
    selecting a stimulation channel for delivering a data stimulation signal to one or more stimulation electrodes, the data stimulation signal based, at least in part, on the audio signal input;
    selecting one or more desensitization channels associated with one or more stimulation electrodes spatially adjacent to, and having spatial channel interaction with, the one or more stimulation channel stimulation electrodes;
    delivering one or more non-data desensitization signals on the one or more desensitization channels during a desensitization period before delivery of the data stimulation signal, wherein the non-data desensitization signals form a ramp shaped sequence; and then
    delivering the data stimulation signal on the stimulation channel while the one or more desensitization channels are still affected by the desensitization signals, wherein cross-talk from the stimulation channel is attenuated on the one or more desensitization channels.

2. A method according to claim 1, further comprising:
    blanking the stimulation channel to prevent stimulation signals during a sensitization period before delivering the data stimulation signal.

3. A method according to claim 1, wherein a psychoacoustic model is used for selecting the stimulation channel.

4. A method according to claim 1, wherein the one or more desensitization signals have an amplitude based on a psychoacoustic model.

5. A method according to claim 1, wherein the one or more desensitization signals have an amplitude based on one or more psychoacoustic measurements.

6. A method according to claim 1, wherein the one or more desensitization signals have an amplitude based on distance between the electrode associated with the desensitization channel and the electrode associated with the stimulation channel.

7. A multi-channel cochlear implant system comprising:
    a microphone for providing an audio input signal;
    an implantable electrode array having a plurality of stimulation electrodes for stimulating audio nerve tissue with electrode stimulation signals; and
    a multichannel stimulation module for generating the electrode stimulation signals including:
        selecting a stimulation channel for delivering a data stimulation signal to one or more stimulation electrodes, the data stimulation signal based, at least in part, on the audio input signal,
        selecting one or more desensitization channels associated with one or more stimulation electrodes spatially adjacent to, and having spatial channel interaction with, the stimulation channel stimulation electrodes,
    delivering one or more non-data desensitization signals on the one or more desensitization channels during a desensitization period before delivery of the data stimulation signal, wherein non-data desensitization signals form a ramp shaped sequence; and then
    delivering the data stimulation signal on the stimulation channel while the one or more desensitization channels are still affected by the desensitization signals, wherein cross-talk from the stimulation channel is attenuated on the one or more desensitization channels.

8. A device according to claim 7, wherein generating the electrode stimulation signals includes blanking the stimulation channel to prevent stimulation signals during a sensitization period before delivering the data stimulation signal.

9. A device according to claim 7, wherein a psychoacoustic model is used for selecting the stimulation channel.

10. A device according to claim 7, wherein the one or more desensitization signals have an amplitude based on a psychoacoustic model.

11. A device according to claim 7, wherein the one or more desensitization signals have an amplitude based on one or more psychoacoustic measurements.

12. A device according to claim 7, wherein the one or more desensitization signals have an amplitude based on distance between the electrode associated with the desensitization channel and the electrode associated with the stimulation channel.

13. A computer program product in a computer readable storage medium for delivering stimulation signals in a multi-channel cochlear implant system, the cochlear implant system including a microphone for providing an audio input signal, an implantable electrode array having a plurality of stimulation electrodes for stimulating audio nerve tissue with electrode stimulation signals, and a multichannel stimulation module for generating the electrode stimulation signals, the product comprising:
  program code for selecting a stimulation channel for delivering a data stimulation signal to one or more stimulation electrodes, the data stimulation signal based, at least in part, on the audio input signal;
  program code for selecting one or more desensitization channels associated with one or more stimulation electrodes spatially adjacent to, and having spatial channel interaction with, the one or more stimulation channel stimulation electrodes;
  program code for delivering one or more non-data desensitization signals on the one or more desensitization channels during a desensitization period before delivery of the data stimulation signal, wherein the non-data desensitization signals form a ramp shaped sequence; and then
  program code for delivering the data stimulation signal on the stimulation channel while the one or more desensitization channels are still affected by the desensitization signals, wherein cross-talk from the stimulation channel is attenuated on the one or more desensitization channels.

14. A product according to claim 13, further comprising:
  program code for blanking the stimulation channel to prevent stimulation signals during a sensitization period before delivering the data stimulation signal.

15. A product according to claim 13, wherein a psychoacoustic model is used for selecting the stimulation channel.

16. A product according to claim 13, wherein the one or more desensitization signals have an amplitude based on a psychoacoustic model.

17. A product according to claim 13, wherein the one or more desensitization signals have an amplitude based on one or more psychoacoustic measurements.

18. A product according to claim 13, wherein the one or more desensitization signals have an amplitude based on distance between the electrode associated with the desensitization channel and the electrode associated with the stimulation channel.

* * * * *